United States Patent

Yih-Jong

Patent Number: 5,382,222
Date of Patent: Jan. 17, 1995

[54] MASSAGING DEVICE

[76] Inventor: Chang Yih-Jong, P.O. Box 82-144, Taipei, Taiwan, Prov. of China

[21] Appl. No.: 987,607
[22] Filed: Dec. 9, 1992
[51] Int. Cl.$^6$ ............................................. A61H 7/00
[52] U.S. Cl. ................................. 601/135; 601/137; 601/15
[58] Field of Search ............... 128/24.3, 41, 44, 57, 128/59–62 R, 67; 600/9, 15

[56] References Cited

U.S. PATENT DOCUMENTS

| | | | |
|---|---|---|---|
| 676,604 | 6/1901 | Fritze | 128/57 |
| 1,491,016 | 4/1924 | McGowan et al. | 128/62 R |
| 2,075,413 | 3/1937 | Welker | 128/62 R |
| 2,168,842 | 8/1939 | Kesteven et al. | 128/61 X |
| 4,210,134 | 7/1980 | Okazaki et al. | 128/67 X |
| 4,722,326 | 2/1988 | Ruderian | 128/57 X |
| 4,744,350 | 5/1988 | Sato | 128/57 |
| 4,787,374 | 11/1988 | De Yarman | 128/67 X |
| 4,846,159 | 7/1989 | Antai et al. | 128/44 X |
| 4,944,747 | 7/1990 | Newth et al. | 128/60 X |

FOREIGN PATENT DOCUMENTS

| | | | |
|---|---|---|---|
| 0044107 | 1/1982 | European Pat. Off. | 128/62 R |
| 398922 | 9/1933 | United Kingdom | 128/62 R |

Primary Examiner—Robert A. Hafer
Assistant Examiner—Brian E. Hanlon
Attorney, Agent, or Firm—Alfred Lei

[57] ABSTRACT

A massaging device including a massaging pad having a spherical surface on which there are a recess and a plurality of hollow protuberances around the recess, a plurality of magnets each mounted into one of the hollow protuberances and the recess, a bottom cover mounted on the bottom cover of the massaging pad, and a retainer having a chain engaged with the hook of massaging pad, whereby the device may be conveniently used to scrape certain parts of the body to obtain relief from nausea or sunstroke, or massage the palm or sole.

1 Claim, 5 Drawing Sheets

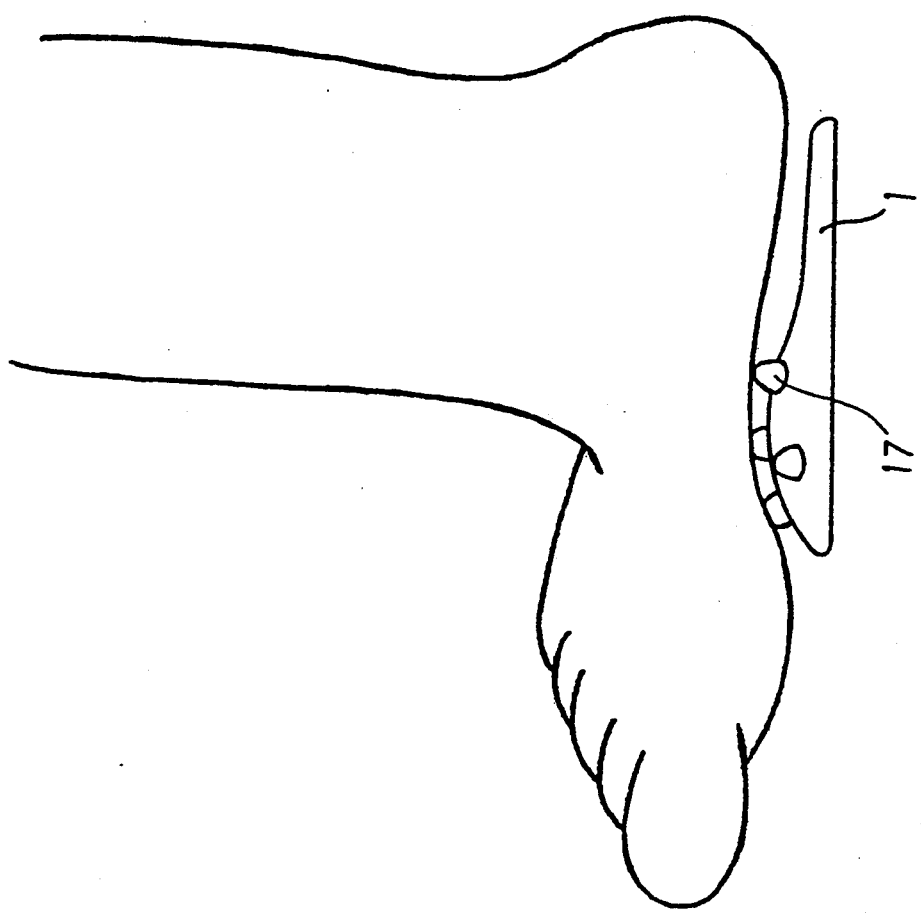

MASSAGING DEVICE

BACKGROUND OF THE INVENTION

Heretofore, there are various hand massage devices for massaging parts of the body on the market. However, such massage devices cannot provide sufficient stimulation and so they can only be used for finger massage, not for veins and vital points. Furthermore, there is a ball massager which is provided with magnetic protuberances for massage and magnetic remedy on sale, but this massager is too heavy and inconvenient in use.

Therefore, it is an object of the present invention to provide a massaging device which may obviate and mitigate the above-mentioned drawbacks.

SUMMARY OF THE INVENTION

This invention relates to a massaging device.

It is the primary object of the present invention to provide a massaging device which It is another object of the present invention to provide a massaging device which may be used to scrape certain parts of the body to obtain relief from nausea or sunstroke.

It is still another object of the present invention to provide a massaging device which may be used to massage the palm or sole.

It is still another object of the present invention to provide a massaging device which is simple in structure.

It is a further object of the present invention to provide a massaging device which is low in cost.

Other objects and merits and a fuller understanding of the present invention will be obtained by those having ordinary skill in the art when the following detailed description of the preferred embodiment is read in conjunction with the accompanying drawings.

BRIEF DESCRIPTION OF THE DRAWINGS

FIG. 7 is a third working view of the present invention.

DETAILED DESCRIPTION OF THE PREFERRED EMBODIMENT

Figure 1:
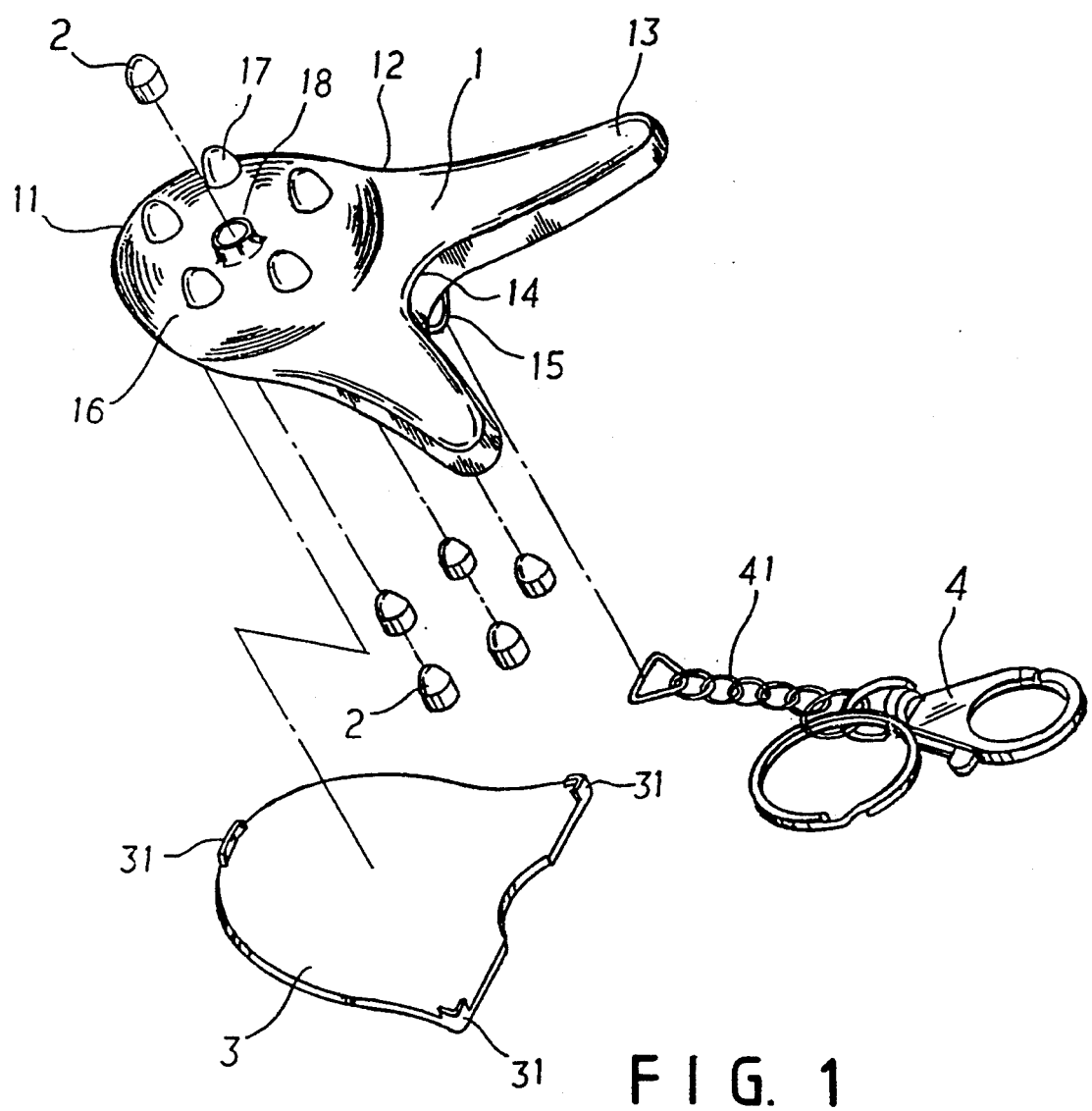
FIG. 1 is an exploded view of the present invention.

With reference to the drawings and in particular to FIG. 1 thereof, the present invention mainly comprises a massaging pad 1, a plurality of magnets 2, a bottom cover 3, and a retainer 4. The massaging pad 1 is formed with a curved head 11 which extends along two curved sides 12 to form two arms 13. The two arms 13 intersect at a curved recess 14 under which there is a hook 15. The head 11 is formed with a partial spherical surface 16 on which there are a recess 18 at the center and a plurality of hollow protuberances 17 around the recess 18. The bottom cover 3 has a plurality of tenons (31) adapted to engage with the bottom of the massaging pad 1.

Figure 2:
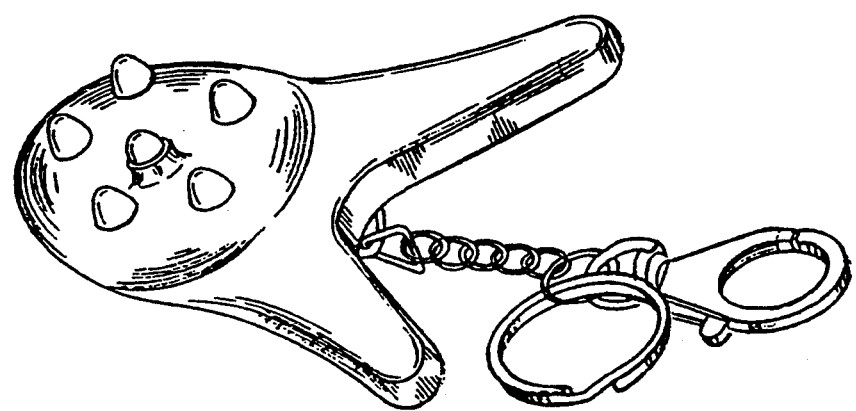
FIG. 2 is a perspective view of the present invention.
Figure 3:
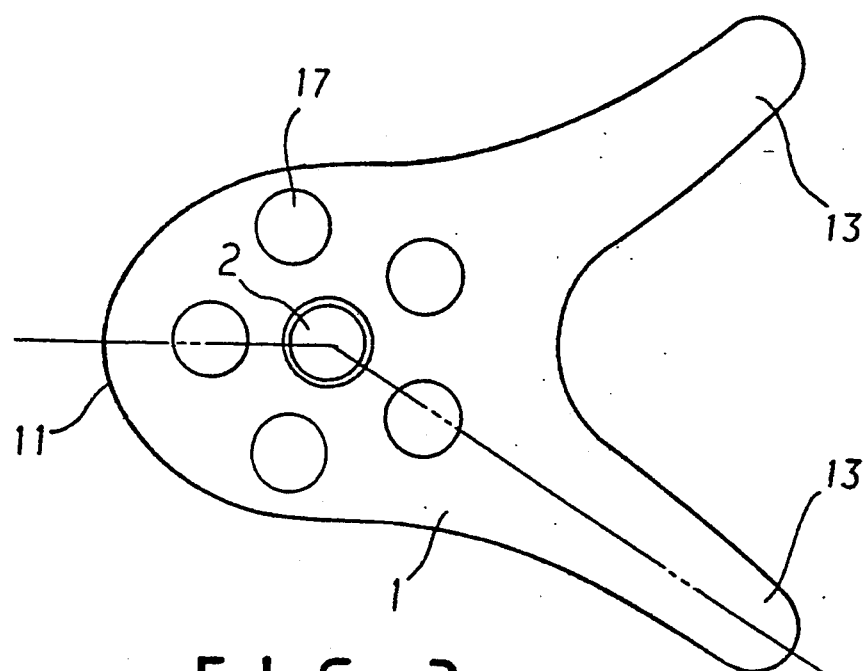
FIG. 3 is a top view of the present invention.
Figure 4:
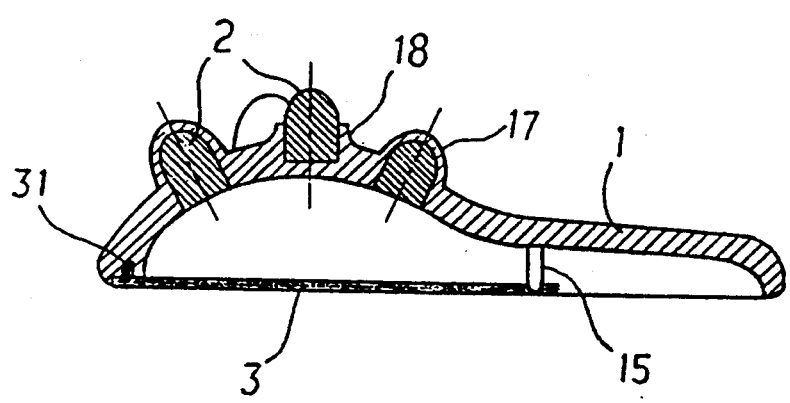
FIG. 4 is a sectional view of the present invention.

In assembly, first embed a magnet 2 in each of the hollow protuberances 17 and the recess 18 and engage the bottom cover 3 with the bottom of the massaging pad 1. Then, connect the chain 41 of the retainer 4 (see FIG. 2). FIG. 3 shows a top view of the massaging pad 1.

Figure 5:
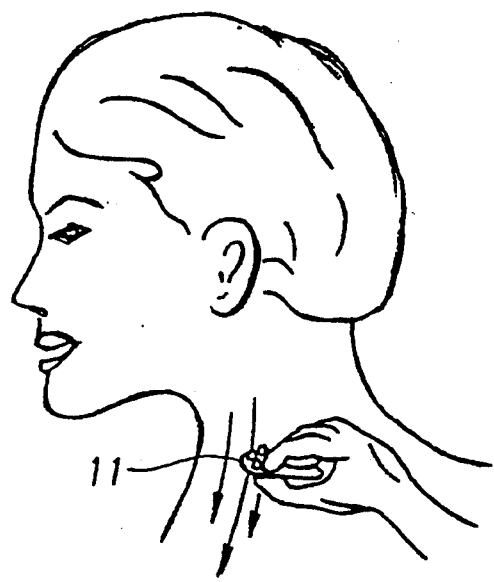
FIG. 5 is a first working view of the present invention.

FIG. 5 shows a first working view of the present invention. As illustrated, the present invention is used to scrape certain parts of the body to obtain relief from nausea or sunstroke.

Figure 6:
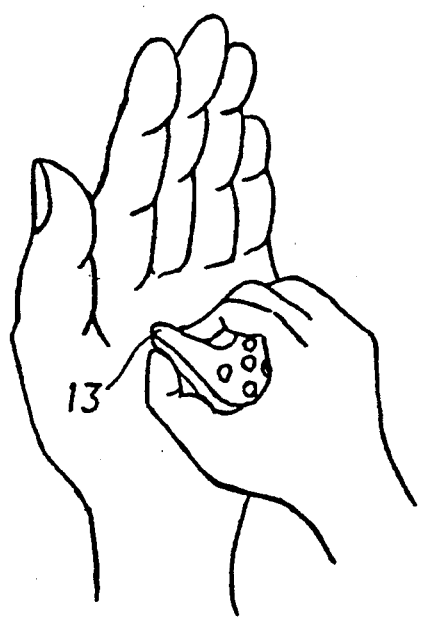
FIG. 6 is a second working view of the present invention.

FIG. 6 shows a second working view of the present invention. As may be seen, the present invention is used to massage the vital points of the palm.

FIG. 7 shows a third working view of the present invention. As shown, the present invention is used to massage the vital points of the sole.

Although the present invention has been described with a certain degree of particularity, it is understood that the present disclosure is made by way of example only and that numerous changes in the detail of construction and the combination and arrangement of parts may be resorted to without departing from the spirit and scope of the invention as hereinafter claimed.

I claim:

1. A massaging device comprising:
   a massaging pad having a curved head portion and two curved side portions extending from said head portion, said two curved side portions forming two elongated arms which intersect at a curved V-shaped recess;
   said head portion having a partially spherical surface with a recess at the center of said surface, said head portion having a plurality of hollow protuberances spaced about said recess, wherein said recess and each of said hollow protuberances contains a magnet; and
   a bottom cover having a plurality of tenons engaging with a bottom of said massaging pad.